United States Patent [19]  
Durette et al.

[11] Patent Number: 4,526,999  
[45] Date of Patent: Jul. 2, 1985

[54] LIPOXYGENASE INHIBITORS

[75] Inventors: Philippe L. Durette, New Providence; Timothy F. Gallagher, Metuchen, both of N.J.

[73] Assignee: Merck & Co., Inc., Rahway, N.J.

[21] Appl. No.: 488,497

[22] Filed: Apr. 25, 1983

[51] Int. Cl.³ .................. C07C 35/20; C07C 43/18
[52] U.S. Cl. .................. 514/549; 260/404; 260/408; 260/410; 260/410.5; 560/101; 560/102; 560/123; 560/125; 560/126; 560/128; 564/123; 564/163; 564/164; 564/166; 568/591; 568/592; 568/669; 568/670; 568/704; 568/715; 568/774; 568/821; 514/715; 514/729; 514/826; 514/929
[58] Field of Search ............ 568/821, 715, 583, 670, 568/704, 591, 592, 669, 774; 260/410.9 R, 408, 410, 410.5; 560/102, 101, 125, 126, 128, 231; 564/123, 191, 163, 164, 166, 171

[56] References Cited

U.S. PATENT DOCUMENTS 3,993,674  11/1976  Schaub et al. .................. 568/821

FOREIGN PATENT DOCUMENTS 1007627  10/1965  United Kingdom .................. 568/821

OTHER PUBLICATIONS

D. Bailey et al, Ann Rpts. Med. Chem., 17, 203–217, (1982).  
R. C. Murphy et al., PNAS, USA, 76, 4275, (1979).  
J. L. Humes et al., J. Biol. Chem., 257, 1591, (1982).  
H. R. Morris et al., Prostagand.  
M. E. Vol'pin et al., Zh. Obsh. Khim., 29, s855, (1959).

Primary Examiner—Werren B. Lone  
Attorney, Agent, or Firm—Donald J. Perrella; Hesna J. Pfeiffer

[57] ABSTRACT

Compounds of the Formula I:

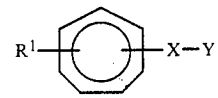

and pharmaceutically acceptable salts thereof are inhibitors of leukotriene biosynthesis. These compounds inhibit lipoxygenase, thus preventing the metabolism of arachidonic acid to the leukotrienes. These compounds are thus useful in the treatment of asthma, allergic disorders, inflammation, skin diseases and certain cardiovascular disorders.

7 Claims, No Drawings

LIPOXYGENASE INHIBITORS

BACKGROUND OF THE INVENTION

This invention is directed to new chemical compounds, especially useful as inhibitors of lipoxygenase enzyme systems. Lipoxygenase controls the biosynthesis of the class of compounds known as leukotrienes. Inhibition of lipoxygenase therefore prevents or diminishes the adverse effects of the leukotrienes in a human subject.

The leukotrienes are a novel group of biologically active mediators derived from arachidonic acid through the action of lipoxygenase enzyme systems. The leukotrienes play an important role in inducing allergic reactions, such as asthma, allergic bronchitis or allergic rhinitis in man. One of the leukotrienes ($B_4$) contributes to both inflammation and allergic reactions in man.

There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biological activity known as slow reacting substances of anaphylaxis. They are potent smooth muscle contracting agents, particularly on respiratory smooth muscle but also on other tissues (e.g., gall bladder). In addition, they promote mucous production, modulate vascular permeability changes and are potent inflammatory agents in human skin.

The most important compound in the second group of leukotrienes is leukotriene $B_4$, a dihydroxy fatty acid derived from leukotriene $A_4$. This compound is a potent chemotactic agent for neutrophils and eosinophils. When injected in vivo, in addition to promoting the accumulation of leukocytes, leukotriene $B_4$ is also a potent hyperalgesic agent and can modulate vascular permeability changes through a neutrophil dependent mechanism. Both groups of leukotrienes are formed following oxygenation of arachidonic acid through the action of the 5-lipoxygenase enzyme. See D. Bailey and F. Casey, *Ann. Rpts. Med. Chem.* 17 203 (1982).

Leukotrienes can also mediate other diseases. These include psoriasis, atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative ionotropic effects on the myocardium. In addition, leukotrienes are important mediators of inflammatory diseases through their ability to modulate leukocyte and lymphocyte function.

SUMMARY OF THE INVENTION

This invention is directed to novel compounds of the Formula I:

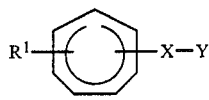

and pharmaceutically acceptable salts thereof wherein the various substituents are as defined herein below.

This invention provides novel compounds that act as inhibitors of lipoxygenase, thus preventing the synthesis of the leukotriene $C_4$, $D_4$ and $E_4$ and also leukotrien $B_4$.

This invention also provides a method of treatment for disease states caused by the synthesis of the leukotrienes $C_4$, $D_4$, $E_4$ and $F_4$, as well as leukotriene $B_4$, in a human subject. This method comprises administering to said subject an effective amount of a compound of Formula I combined with an appropriate pharmaceutical carrier.

DETAILED DESCRIPTION OF THE INVENTION

This invention is directed to novel compounds of the Formula I:

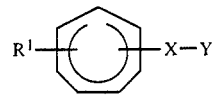

wherein:

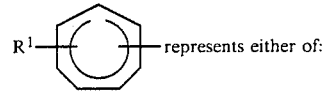  represents either of:

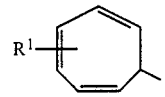

or

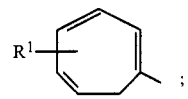

and:
X is

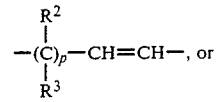

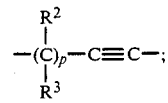

Y is

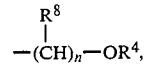

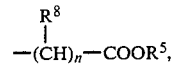

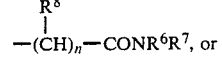

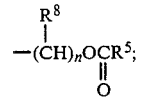

$R^1$, $R^2$ and $R^3$ are each independently: hydrogen, halogen, loweralkyl, alkyl, hydroxy, loweralkoxy, amino, monoloweralkyl substituted amino, diloweralkyl substituted amino, benzyl, benzyl substituted with one or more $R^9$, aralkyl, aralkyl substituted with one or more $R^9$, phenyl, phenyl substituted with one or more $R^9$;

$R^4$ is hydrogen, lower alkyl;

$R^5$ is $C_1$-$C_7$alkyl;

$R^6$, $R^7$ and p is an integer of from 0–4;

and pharmaceutically acceptable salts thereof.

SCHEME I

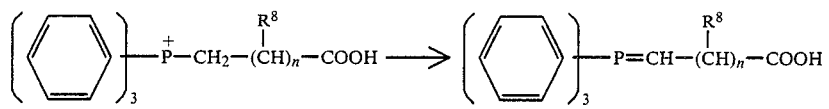

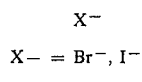

IV             III

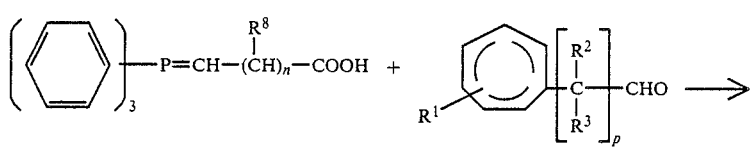

III             II

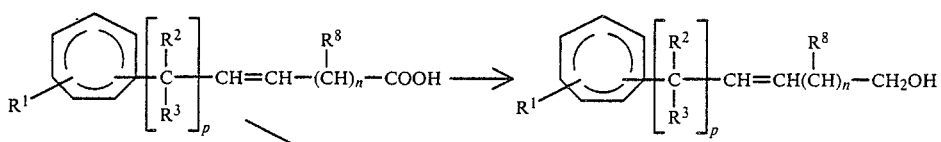

V              VI

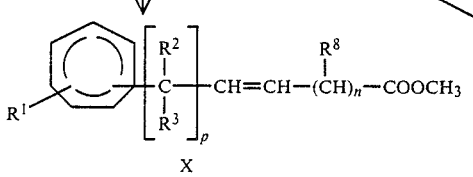

X

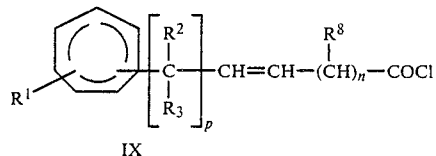

IX

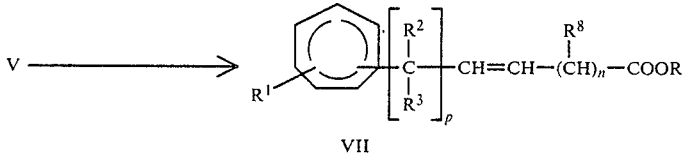

VII

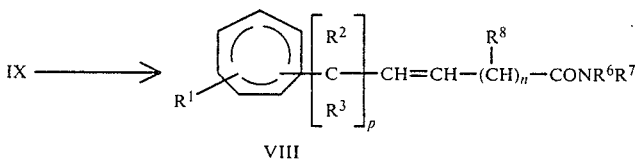

VIII $R^8$ are each independently hydrogen or $C_1$-$C_6$ loweralkyl;

$R^9$ is alkyl, halogen, hydroxy, loweralkoxy, amino, nitro, trihaloalkyl;

n is an integer of from 1–10;

As illustrated in Scheme I, the compounds of the present invention are prepared by reaction of the appropriate aldehyde (II) with the appropriate phosphorane (III) derived by treatment of the appropriate substituted-alkyl triphenylphosphonium halide (IV) (preferably, bromide or iodide) in a solvent, such as diethyl ether, tetrahydrofuran, dimethyl sulfoxide, or alcohol, with a strong base (e.g., an organolithium compound, such as n-butyllithium or phenyllithium; sodium hydride; or sodium amide) or a moderately strong base, such as a metal alkoxide (e.g., sodium ethoxide or potassium tert-butoxide). The Wittig reaction is performed at a temperature of from −25° C. to 100° C. for from 30 min. to 24 hr. The starting aldehyde is either known or can be made by known procedures.

Conversion of the derived alkenylalkanoic acid (V, R=COOH) into the alkenylalkanol (VI) is achieved by metal hydride reduction, i.e., treatment of the acid with a metal hydride, such as lithium borohydride, sodium borohydride, lithium aluminum hydride, diborane, or the like, in a solvent, such as diethyl ether, tetrahydrofuran, dimethoxyethane, diglyme, p-dioxane, ethanol, ethanol, isopropanol, or the like, at a temperature of from 0° to 85° C. for from 30 minutes to 24 hours.

The acids (V) are converted into the methyl ester (X) derivatives either by (a) treatment with diazomethane in a solvent such as diethyl ether, dichloromethane, tetrahydrofuran, or the like at a temperature of from −10° to 25° C. for from 5 minutes to 1 hour; or (b) treatment with methanol in the presence of an acid catalyst such as hydrogen chloride, concentrated sulfuric acid, or acidic ion-exchange resin, in particular, with an exchange resin containing sulfonic acid groups, e.g., Amberlite IR-120 (resins of styrene containing strongly acidic sulfonyl groups) or Dowex-50 (polystyrene sulfonic acids) at reflux temperature for from 12 to 48 hours; or (c) treatment of an alkali salt, such as sodium salt, with a methylating agent, such as iodomethane, in a solvent such as N,N-dimethylformamide, hexamethylphosphoric triamide, or the like, at room temperature for from 15 minutes to 24 hours.

The $C_{2-7}$ ester derivatives (VII) are prepared by treatment of an alkali salt of the acid, (V, R=COOM) such as a potassium (M=K) or sodium (M=Na) salt, with an alkylating agent, such as an iodoalkane or bromoalkane, in a solvent such as N,N-dimethylformamide, hexamethylphosphoric triamide, or the like, at room temperature for from 15 minutes to 24 hours.

The acids (V) are converted into their amide derivatives (VIII) by first converting them into their acid chlorides, (IX) by treatment with a chlorinating agent such as thionyl chloride, oxalyl chloride, or the like, in a solvent such as diethyl ether, dichloromethane, tetrahydrofuran, or the like in the presence of an acid acceptor, such as pyridine, triethylamine, 4-dimethylaminopyridine, or the like, at a temperature of from −25° to 25° for from 5 minutes to several hours. These acid chlorides (IX) are then treated with the appropriate primary or secondary amine in a solvent such as diethyl ether, dichloromethane, tetrahydrofuran, or the like, optionally in the presence of an acid acceptor, such as pyridine, triethylamine, 4-dimethylaminopyridine, at a temperature of from −25° to 25° for from 5 minutes to 24 hours.

In the case where a carboxyalkyl triphenylphosphonium salt is employed in the Wittig reaction, a carboxyalkylalkene (V) is obtained.

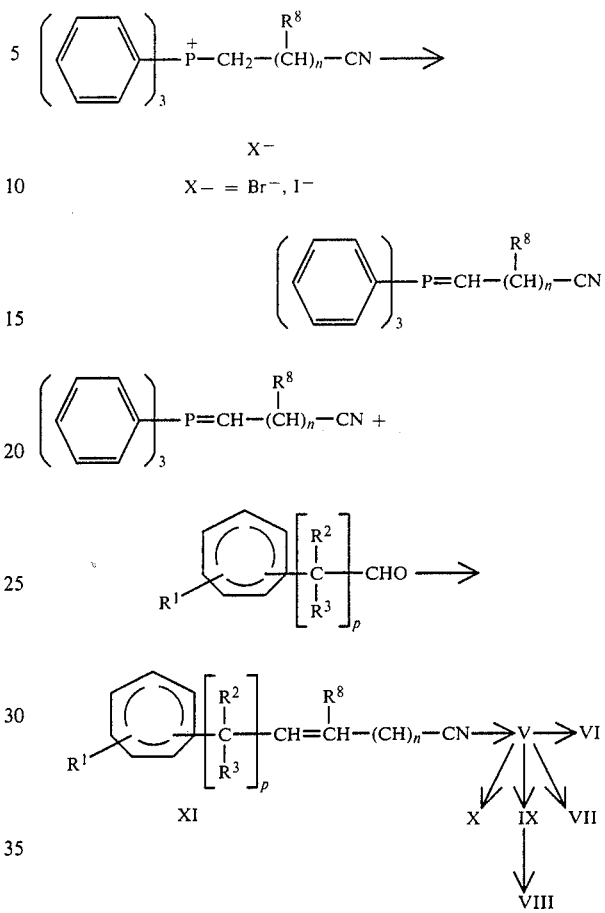

In the case where a cyanoalkyl triphenylphosphonium salt is used, as illustrated in Scheme II, a cyanoalkylalkene (XI) is obtained.

The cyanoalkylalkene (XI) is converted into the alkenylalkanol (VI) by first hydrolyzing it to the alkenylalkanoic acid (V) by treatment with aqueous alkali hydroxide, such as sodium or potassium hydroxide in a solvent, such as methanol, ethanol, or the like, at a temperature of from 50° to 100° C. for from 12 to 73 hours. The acid is then reduced to the alcohol (VI) as described above.

The Formula I compounds are potent inhibitors of the 5-lipoxygenase pathway of arachidonic acid metabolism and have little or no inhibiting effect on the cyclooxygenase pathway of arachidonic acid metabolism.

The compounds of Formula I are active as inhibitors of the biosynthesis of both leukotriene $B_4$, as well as leukotrienes $C_4$, $D_4$, and $E_4$, the active elements of slow reacting substance of anaphylaxis (SRS-A). This inhibition of the biosynthesis of leukotrienes indicates that the compositions would be useful to treat, prevent or ameliorate, in mammals and especially in humans (1) pulmonary conditions including diseases such as asthma, (2) allergies and allergic reactions such as allergic rhinitis, contact dermatitis, and allergic conjunctivitis. The compounds of Formula I are also useful as anti-inflammatory and analgesic agents; agents for the treatment of skin conditions, such as psoriasis; and cardiovascular conditions, such as angina.

The ability of the compounds of Formula I to inhibit leukotriene synthesis was determined by their ability to: (a) inhibit rat basophilic leukemia (RBL-1) 5-lipoxygenase; (b) inhibit the synthesis and/or release of leukotriene $C_4$ in vitro from mouse peritoneal macrophages; (c) inhibit the synthesis and/or release of leukotriene $B_4$ from rat peritonal polymorphonuclear leukocytes; and (d) inhibit ovalbumin-induced contractions of sensitized smooth muscle strips. These assays are known to the skilled artisan. See for example; (a) R. C. Murphy et al, *PNAS USA,* 76 4275 (1979); (b) J. L. Humes et al., *J. Biol. Chem.,* 257 1591 (1982); (c) E. A. Ham et al., *PNAS USA,* in press (1983); and (d) H. R. Morris et al., *Prostaglandins,* 19 371 (1980).

The magnitude of a prophylactic or therapeutic dose of a compound of Formula I will, of course, vary with the nature of the severity of the condition to be treated and with the particular compound of Formula I and its route of administration. In general, the daily dose range lies within the range of from about 10 μg to about 50 mg, preferably from about 1 mg to about 25 mg, per kg body weight of a mammal.

The pharmaceutical compositions of the present invention comprise a compound of Formula I as an active ingredient, and may also contain a pharmaceutically acceptable carrier and optionally other therapeutic ingredients. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of Formula I are conveniently delivered in the form of an aerosol spray presentation from pressurized packs of a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount. These inhalation formulations may be administered in doses ranging from about 0.1 μg to about 200 μg, administered as necessary to provide therapeutic relief.

Pharmaceutical compositions of the present invention suitable for oral administration and by inhalation in the case of asthma therapy may be presented as discrete units such as capsules, cachets or tablets, each containing a predetermined amount of the active ingredient, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

The following examples illustrate the present invention without, however, limiting the same thereto. Temperatures are shown in 0° C. and are uncorrected.

EXAMPLE 1

7-(1',3',5'-Cycloheptatrien-7'-yl)-7-methyl-cis-5-octen-1-ol

Step A:
7-(1',3',5-Cycloheptatrien-7'-yl)-7-methyl-cis-5-octenoic acid

A mixture of 769 mg (16.0 mmol) of 50% sodium hydride in mineral oil and 18 ml of dimethyl sulfoxide was stirred under nitrogen for 1.5 hours at 75°. The resulting mixture was cooled to ambient temperature, and a solution of (4-carboxybutyl)triphenylphosphonium bromide (3.55 g, 8.0 mmol) in dimethyl sulfoxide (5 ml) was added. The resulting dark red solution was stirred under nitrogen for 1 hour at room temperature. To this solution was added dropwise with stirring a solution of α-cycloheptatrienylisobutyraldehyde (650 mg, 4.0 mmol) [prepared by the process set forth in M. E. Vol'pin et al., *Zh. Obsh. Khim.,* 29, 2855 (1959)] in dimethyl sulfoxide (10 ml). After 30 minutes, the reaction was quenched by addition to a mixture of 0.2M sodium bisulfate in ice-water and diethyl ether. The aqueous layer was extracted with ether, and the combined organic extracts were washed with water, dried (sodium sulfate) and evaporated. The crude product was chromatographed on a column of silica gel (Merck No. 7734, packed as a slurry in 1:4 ether-hexane). Elution with 1:4 ether-hexane containing 1% acetic acid gave pure 7-(1',3',5'-cycloheptatrien-7'-yl)-7-methyl-cis-5-octenoic acid; yield 670 mg (68%).

Step B:
7-(1',3',5'-Cycloheptatrien-7'-yl)-7-methyl-cis-5-octen-1-ol

A solution of 7-(1',3',5'-cycloheptatrien-7'-yl)-7-methyl-cis-5-octenoic acid (150 mg, 0.61 mmol) in tetrahydrofuran (8 ml) was treated with lithium aluminum hydride (47 mg) for 1 hour at room temperature. Excess lithium aluminum hydride was decomposed by sequential addition of water (47 μl), 15% aqueous sodium hydroxide (47 μl), and water (141 μl). The mixture was filtered through Celite, the filter washed with tetrahydrofuran, and the combined filtrate and washings evaporated. The residue was taken up in ether, washed with water, and dried (sodium sulfate). The product was purified by chromatography on silica gel (E. Merck No. 7734) (elution with 1:2 ether-hexane); yield 107 mg (76%).

The 200 MHz NMR spectrum in chloroform-d indicated cis-(Z) stereochemistry: 2.25 (q, 2H, C$\underline{H}_2$CH$_2$OH) and 3.68 (q, 2H, C$\underline{H}_2$OH).

EXAMPLE 2

7'-(1',3',5'-Cycloheptatrien-7'-yl)-cis-5-octen-1-ol

Employing the procedure substantially as described in Example 1, but substituting for the α-cycloheptatrienylisobutyraldehyde used in Step A thereof, an equivalent amount of α-cycloheptatrienylpropionaldehyde, there were prepared in sequence:

Step A: 7-(1',3',5'-Cycloheptatrien-7'-yl)-cis-5-octenoic acid

The 300 MHz NMR spectrum in chloroform-d was in accord with the desired structure (indicating cis-stereochemistry).

Step B:
7-(1',3',5'-Cycloheptatrien-7'-yl)-cis-5-octen-1-ol

The 300 MHz NMR spectrum in chloroform-d was in accord with the desired structure (indicating cis-stereochemistry).

EXAMPLE 3

7-(1',3',5'-Cycloheptatrien-7'-yl)-cis-5-hepten-1-ol

Employing the procedure substantially as described in Example 1, but substituting for the α-cycloheptatrienylisobutyraldehyde used in Step A thereof, an equivalent amount of cycloheptatrienylacetaldehyde, there are prepared in sequence:

Step A:
7-(1',3',5'-Cycloheptatrien-7'-yl)-cis-5-heptenoic acid

The 300 MHz NMR spectrum in chloroform-d is in accord with the desired structure (indicating cis-stereochemistry).

Step B:
7-(1',3',5'-Cycloheptatrien-7'-yl-cis-5-hepten-1-ol

The 300 MHz NMR spectrum in chloroform-d is in accord with the desired structure (indicating cis-stereochemistry).

EXAMPLE 4

7-(1',3',5'-Cycloheptatrien-7'-yl)-cis-5-octenoic acid methyl ester

The title compound was obtained by treatment of 7-(1',3',5'-cycloheptatrien-7'-yl)-cis-5-octenoic acid in cold dichloromethane with diazomethane. The 300 MHz NMR spectrum in chloroform-d was in accord with the desired structure: 3.72 (s, 3H, COOC$\underline{H}_3$).

EXAMPLE 5

6-(1',3',5'-Cycloheptatrien-7'-yl)-cis-4-hepten-1-ol

Step A:
5-(1',3',5'-Cycloheptatrien-7'-yl)-3-hexenonitrile

A mixture of 324 mg (6.75 mmol) of 50% sodium hydride in mineral oil and 8 ml of dimethyl sulfoxide was stirred under nitrogen for 1.5 hours at 75°. The resulting mixture was cooled to ambient temperature, and a solution of (3-cyanopropyl)triphenylphosphonium bromide (2.77 g, 6.75 mmol) in dimethyl sulfoxide (10 ml) was added. The resulting dark red solution was stirred under nitrogen for 1 hour at room temperature. To this solution was added dropwise with stirring a solution of α-cycloheptatrienylpropionaldehyde (500 mg, 3.37 mmol) in dimethyl sulfoxide (5 ml). After 1 hour, the reaction was quenched by pouring into a mixture of water and ether. The aqueous layer was extracted with ether, and the combined organic extracts were washed with water, dried (sodium sulfate), and evaporated. The residue was dissolved in a small volume of dichloromethane and the solution applied to a column of silica gel (E. Merck, No. 7734). Elution with 1:20 ether-hexane afforded the pure nitrile; yield 430 mg (64%).

Step B:
6-(1',3',5'-Cycloheptatrien-7'-yl)-cis-4-heptenoic acid 5-(1',3',5'-Cycloheptatrien-7'-yl)-3-hexenonitrile (430 mg, 2.16 mmol) in ethanol (15 ml) was hydrolyzed with 10% aqueous potassium hydroxide (5 ml) for 24 hours at reflux temperature. The mixture was cooled and concentrated and the residue brought to about pH 2 with 2$\underline{N}$ hydrochloric acid. The mixture was partitioned between ether and water, the aqueous layer extracted with ether, the combined organic extracts washed with saturated sodium chloride solution, dried (sodium sulfate), and evaporated. The product was purified by passage through a column of silica gel (Merck No. 7734) (packed as a slurry in 1:4 ether-hexane; elution with 1:4 ether-hexane containing 1% acetic acid); yield 340 mg (72%).

The 300 MHz NMR spectrum in chloroform-d was in accord with the desired structure (indicating cis-stereochemistry).

Step C:
6-(1',3',5'-Cycloheptatrien-7'-yl)-cis-4-hepten-1-ol

A solution of 6-(1',3',5'-cycloheptatrien-7'-yl)-cis-4-heptenoic acid (130 mg, 0.62 mmol) in tetrahydrofuran (10 ml) was treated with lithium aluminum hydride (47 mg) for 1 hour at room temperature. Excess lithium aluminum hydride was decomposed by sequential addition of water (47 µl), 15% aqueous sodium hydroxide (47 µl) and water (141 µl). The mixture was filtered through Celite, the filter washed with tetrahydrofuran, and the combined filtrate and washings evaporated. The residue was dissolved in ether, washed with saturated sodium chloride solution, and evaporated. The product was purified by chromatography on silica gel (E. Merck No. 7734, elution with 1:3 ether-hexane); yield 88 mg (69%).

The 300 MHz NMR spectrum in chloroform-d was in accord with the desired structure (indicating cis-stereochemistry).

EXAMPLE 6

1-(3'-Methoxypropyl)-3-(1',3',5'-cycloheptatrien-7'-yl)-cis-1-butene

To a solution of 6-(1',3',5'-cycloheptatrien-7'-yl)-cis-4-hepten-1-ol (50 mg) in N,N-dimethylformamide (4 ml) was added iodomethane (30 µl). The solution was cooled to ice temperature, and sodium hydride (50% oil dispersion) (23 mg) was added. After 4 hours at room temperature, additional iodomethane (30 µl) and sodium hydride (23 mg) were added, and the mixture was stirred overnight at room temperature. It was then poured into water, extracted with ether and the combined extracts evaporated and coevaporated with methanol. The product was purified by chromatography on silica gel (E. Merck No. 7734, elution with 1:40 ether-hexane); yield 30 mg (56%).

The 60 MHz NMR spectrum in chloroform-d was in accord with the desired structure: 3.3 (s, 3H, OC$\underline{H}_3$).

EXAMPLE 7

1-(3'-Acetyloxypropyl)-3-(1',3',5'-cycloheptatrien-7'-yl)-cis-1-butene 6-(1',3',5'-Cycloheptatrien-7'-yl)-cis-4-hepten-1-ol (20 mg) was treated with acetic anhydride and pyridine overnight at room temperature. The mixture was evaporated and coevaporated several times with toluene. Chromatography on silica gel (E. Merck No. 7734; elution with 1:10 ether-hexane) afforded the pure acetate; yield 21 mg (88%).

Claims to the invention follow.

What is claimed is:

1. Compounds having the formula:

wherein:

 represents either of:

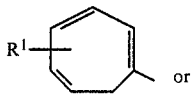 or

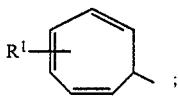 ;

and:

X is

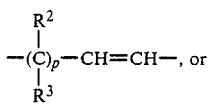

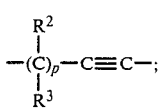 ;

Y is

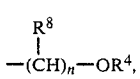 ,

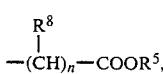 ,

 or

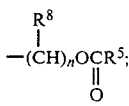 ;

$R^1$, $R^2$ and $R^3$ are each independently: hydrogen, halogen, loweralkyl, alkyl, hydroxy, loweralkoxy, amino, monoloweralkyl substituted amino, diloweralkyl substituted amino, aralkyl, aralkyl substituted with one or more $R^9$, phenyl, phenyl substituted with one or more $R^9$;

$R^4$ is hydrogen, lower alkyl;

$R^5$ is $C_1$–$C_7$alkyl;

$R^6$, $R^7$ and $R^8$ are each independently hydrogen or $C_1$–$C_6$ loweralkyl;

$R^9$ is alkyl, halogen, hydroxy, loweralkoxy, amino, nitro, trihaloalkyl;

n is an integer of from 1–10;

p is an integer of from 0–4; and pharmaceutically acceptable salts thereof.

2. The compounds of claim 1 wherein X is:

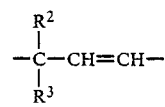

3. The compounds of claim 1 wherein X is:

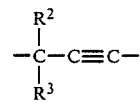

4. The compounds of claim 1:

7-(1′,3′,5′-Cycloheptatrien-7′-yl)-7-methyl-cis-5-octen-1-ol;

7′-(1′,3′,5′-Cycloheptatrien-7′-yl)-cis-5-octen-1-ol;

7-(1′,3′,5′-Cycloheptatrien-7′-yl)-cis-5-hepten-1-ol;

7-(1′,3′,5′-Cycloheptatrien-7′-yl)-cis-5-octenoic acid methyl ester;

6-(1′,3′,5′-Cycloheptatrien-7′-yl)-cis-4-hepten-1-ol;

1-(3′-Methoxypropyl)-3-(1′,3′,5′-cycloheptatrien-7′-yl)-cis-1-butene;

1-(3′-Acetyloxypropyl)-3-(1′,3′,5′-cycloheptatrien-7′-yl)-cis-1-butene.

5. A composition containing a compound of claim 1 and a pharmaceutical carrier.

6. A method of inhibiting the actions of lipoxygenase in mammals, especially humans, which comprises administering to said mammals a pharmaceutically effective amount of the composition of claim 5.

7. A method of treating asthma, allergic disorders, inflammation, skin diseases and cardiovascular disorders in humans which comprises administering to said humans a pharmaceutically effective amount of the composition of claim 5.

* * * * *